United States Patent [19]

Kinsho et al.

[11] Patent Number: 5,547,606

[45] Date of Patent: Aug. 20, 1996

[54] SILACYCLOHEXANE COMPOUND, A METHOD OF PREPARING IT AND A LIQUID CRYSTAL COMPOSITION CONTAINING IT

[75] Inventors: Takeshi Kinsho; Tatsushi Kaneko; Takaaki Shimizu, all of Joetsu; Tsutomu Ogihara, Kubiki-mura; Ryuichi Saito, Joetsu; Hideshi Kurihara, Yokohama, all of Japan

[73] Assignee: Shin-Etsu Chemical Co., Ltd., Tokyo, Japan

[21] Appl. No.: 322,549

[22] Filed: Oct. 13, 1994

[30] Foreign Application Priority Data

Oct. 14, 1993 [JP] Japan .................................. 5-281883
Aug. 19, 1994 [JP] Japan .................................. 6-218170

[51] Int. Cl.⁶ ........................ C09K 19/34; C09K 19/30; C07F 7/08; G02F 1/13
[52] U.S. Cl. .............. 252/299.61; 556/406; 252/299.63; 359/103
[58] Field of Search ................ 252/299.63, 299.61; 556/406; 359/103

[56] References Cited

U.S. PATENT DOCUMENTS

| | | | |
|---|---|---|---|
| 2,381,002 | 8/1945 | Patrode et al. ................ | 556/406 X |
| 2,607,791 | 8/1952 | Goodwin ........................ | 556/406 X |
| 4,937,364 | 6/1990 | Okinoshima .................... | 556/406 |
| 4,965,367 | 10/1990 | Baney et al. ................... | 548/110 |
| 4,985,565 | 1/1991 | Baney et al. ................... | 548/110 |

FOREIGN PATENT DOCUMENTS

| | | |
|---|---|---|
| 0102047 | 3/1984 | European Pat. Off. . |
| 0280902 | 9/1988 | European Pat. Off. . |
| 0355008 | 2/1990 | European Pat. Off. . |
| 4014488 | 11/1991 | Germany . |

*Primary Examiner*—C. H Kelly
*Attorney, Agent, or Firm*—Townsend & Banta

[57] ABSTRACT

A silacyclohexane compound represented by the following general formula (I).

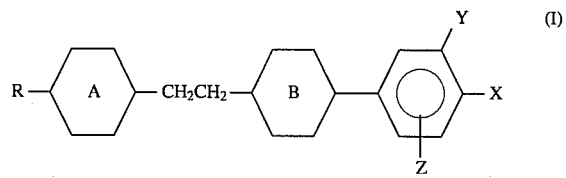

In this formula, R denotes hydrogen, a linear-chain alkyl group with a carbon number of 1–10, a branched-chain alkyl group with a carbon number of 3–8, an alkoxyalkyl group with a carbon number of 2–7, a fluoroalkyl group with a carbon number of 1–10 in which one or two hydrogen atoms are substituted by florine atom(s), or an alkenyl group with a carbon number of 2–8. For the groups

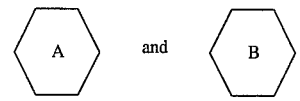

at least one of these is a trans-1-sila-1,4-cyclohexylene or trans-4-sila-1,4-cyclohexylene group whose silicon at position 1 or position 4 has a substitutional group(s) of H, F, Cl or $CH_3$, and the other denotes a trans-1,4-cyclohexylene group. X denotes a CN, F, Cl, $CF_3$, $CF_2Cl$, CHFCl, $OCF_3$, $OCHF_2$, $OCF_2Cl$, OCHFCl, R or OR group (R is the same as defined earlier). Y denotes H or F. Z denotes H or F.

4 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the Invention

This invention relates to a new silacyclohexane compound, a method of preparing it, and a liquid crystal composition which contains it as well as a liquid crystal display element which contains said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

Properties required of the liquid crystal substance used in these liquid crystal displays are somewhat different depending on the display mode. However, a wide liquid crystal temperature range and stability against moisture, air, light, heat, electric fields, etc. are commonly required in all display methods. Furthermore, it is desirable for the liquid crystal material to have a low viscosity, and also to have a short address time, low threshold voltage and high contrast in the cell(s).

Currently, there is no single compound which satisfies all of these requirements. In practice, liquid crystal mixtures are obtained by mixing several to more than ten liquid crystal compounds and liquid crystal like compounds. Because of this, it is also important that components of a liquid crystal composition mix easily each other.

Among liquid crystal compounds which can be components for these, one of the basic components conventionally known which controls the electro-optical performance is a compound which has a so-called cyclohexyl ring-ethylene-cyclohexyl ring-phenyl ring structure (CECP structure) such as those shown by the following general formulas:

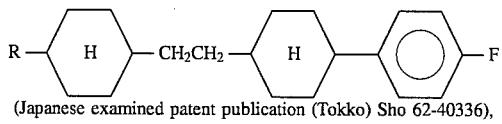
(Japanese examined patent publication (Tokko) Sho 62-40336),

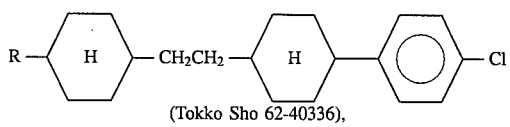
(Tokko Sho 62-40336),

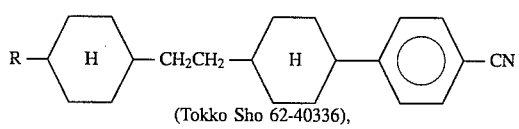
(Tokko Sho 62-40336),

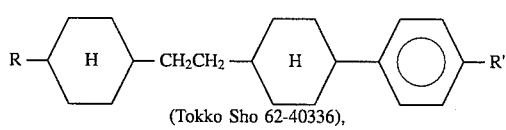
(Tokko Sho 62-40336),

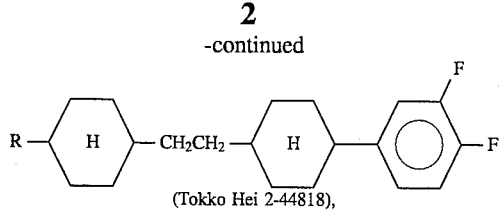
(Tokko Hei 2-44818),

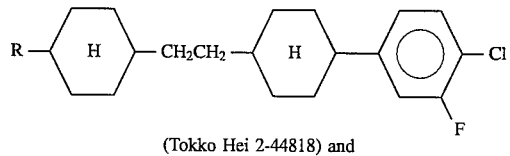
(Tokko Hei 2-44818) and

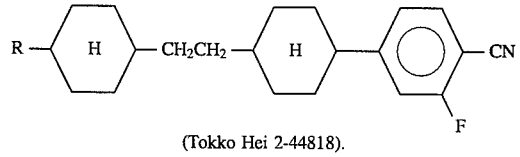
(Tokko Hei 2-44818).

In recent years, along with the expansion of the applications of liquid crystal displays, the characteristics required of liquid crystal materials are becoming more and more advanced and demanding. In particular, superior characteristics such as a lower driving voltage, a wider temperature range for automobile onboard use and improved low temperature performance, compared with conventional liquid crystal substances, are desired.

BRIEF SUMMARY OF THE INVENTION

From such a viewpoint, this invention is a newly developed liquid crystal substance targeting improvement in characteristics of liquid crystal substances, and its object is to provide a liquid crystal compound containing silacyclohexane rings, which is completely different from the conventional liquid crystal compounds with the cyclohexyl ring-ethylene-cyclohexyl ring-phenyl ring structure (CECP structure).

This invention provides a silacyclohexane compound represented by the following general formula (I).

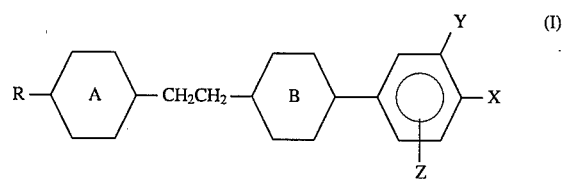

In this formula, R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. For the groups

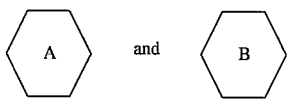

at least one of these is a trans-1-sila-1,4-cyclohexylene or trans-4-sila-1,4-cyclohexylene group whose silicon at position 1 or position 4 has a substitutional group(s) of H, F, Cl or $CH_3$, and the other denotes a trans-1,4-cyclohexylene group. X denotes a CN, F, Cl, $CF_3$, $CF_2Cl$, $CHFCl$, $OCF_3$, $OCHF_2$, $OCF_2Cl$, $OCHFCl$, R or OR group (R is the same as defined in the general formula (1). Y denotes H or F. Z denotes H or F.

This invention also provides a method of preparing the silacyclohexane compound represented by the general formula (I) characterized by carbon-carbon bond formation or carbon-silicon bond formation using a specific organometallic reagent. The preparing methods are listed below.

A method of preparing a silacyclohexane compound using a reaction between an organometallic reagent R-M and a compound

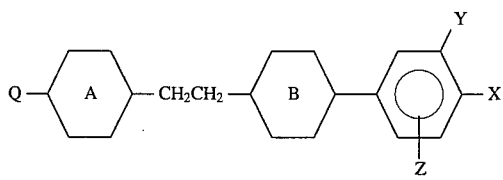

In this formula, M denotes MgP (P denotes a halogen atom), ZnP or Li. R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. Q denotes a halogen atom, or an alkoxy, methanesulfonyl, benzenesulfonyl or p-toluenesulfonyl group. X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F.

A method of preparing a silacyclohexane compound using a reaction between an organometallic reagent

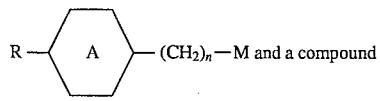

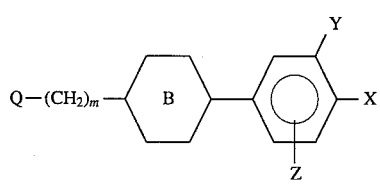

In this formula, M denotes MgP (P denotes a halogen atom), ZnP or Li. R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. Q denotes a halogen atom, alkoxy, methanesulfonyl, benzenesulfonyl or p-toluenesulfonyl group. X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F. n and m are integers 0, 1 or 2 (where n+m=2).

A method of preparing a silacyclohexane compound using a reaction between an organometallic reagent

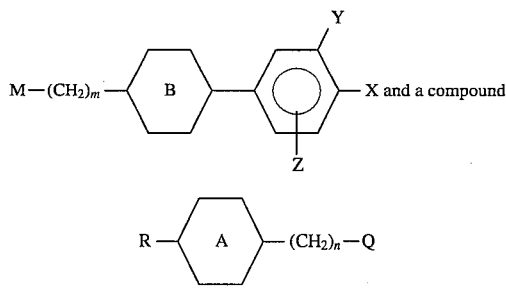

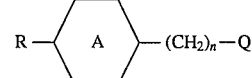

In this formula, M denotes MgP (P denotes a halogen atom), ZnP or Li. R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. Q denotes a halogen atom, or an alkoxy, methanesulfonyl, benzenesulfonyl or p-toluenesulfonyl group. X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F. n and m are integers 0, 1 or 2 (where n+m=2).

A method of preparing a silacyclohexane compound using a reaction between an organometallic reagent

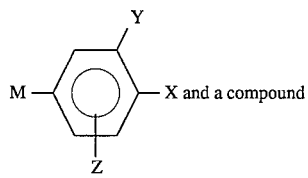

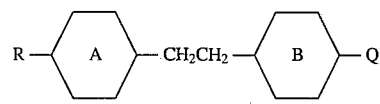

In this formula, M denotes MgP (P denotes a halogen atom), ZnP or Li. R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. Q denotes a halogen atom, or an alkoxy, methanesulfonyl, benzenesulfonyl or p-toluenesulfonyl group. X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F.

A method of preparing a silacyclohexane compound using a reaction between an organometallic reagent

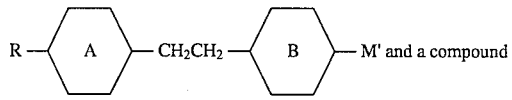

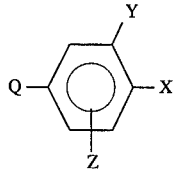

In these formulas, M' denotes MgP (P denotes a halogen atom), ZnP or B(OY') (Y' denotes H or an alkyl group). R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. Q denotes a halogen atom, alkoxy, methanesulfonyl, benzenesulfonyl or p-toluenesulfonyl group. X denotes a CN, F, Cl, CF$_3$, CF$_2$Cl, CHFCl, OCF$_3$, OCHF$_2$, OCF$_2$Cl, OCHFCl, R or OR group. Y denotes H or F. Z denotes H or F.

Furthermore, this invention is a liquid crystal composition characterized by containing the compound represented by the general formula (I) as shown above, as well as a liquid crystal display element using this liquid crystal composition.

The new compounds represented by the general formula (I) are silacyclohexane compounds whose ring structure has at least one trans-1 or 4-trans-silacyclohexane ring, specifically represented by the ring structures shown below:

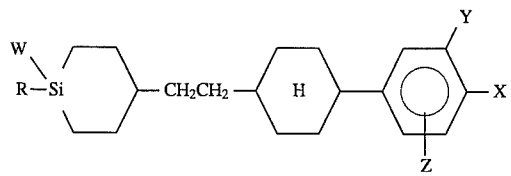

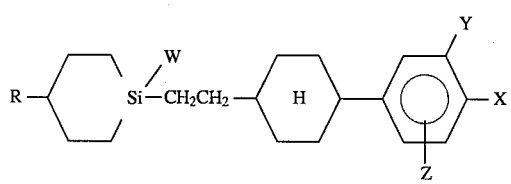

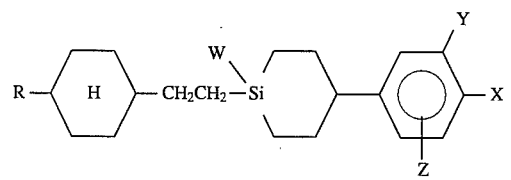

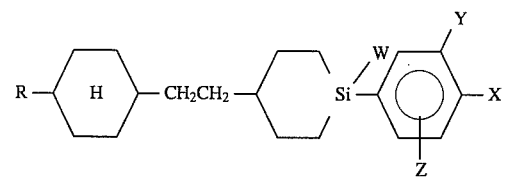

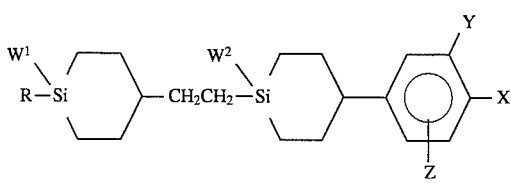

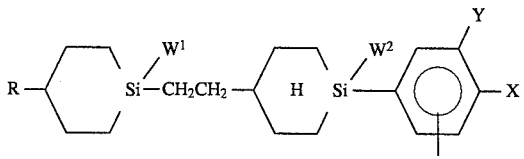

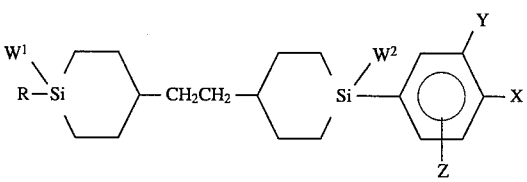

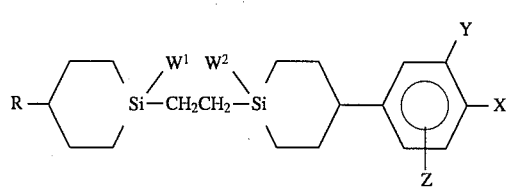

In these formulas, R denotes: a linear-chain alkyl group with a carbon number of 1–10, i.e. a methyl, ethyl, n-propyl, n-butyl, n-pentyl, n-hexyl, n-heptyl, n-octyl, n-nonyl or n-decyl group; or a branched-chain alkyl group with a carbon number of 3–8, i.e. isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group; or an alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl or ethoxypentyl group; or a floroalkyl group with a carbon number of 1–10 in which one or two hydrogen atoms are substituted by florine atoms(s), i.e. a 1-floroethyl, 1-floropropyl, 1-florobutyl, 1-floropentyl, 2-floroethyl, 2-floropropyl, 2-florobutyl, 2-floropentyl, 3-floropropyl, 3-florobutyl, 3-floropentyl, 4-florobutyl, 4-floropentyl, 5-floropentyl, 1,1-difloroethyl, 1,1-difloropropyl, 1,1-diflorobutyl, 1,1-difloropentyl, 2,2-difloroethyl, 2,2-difloropropyl, 2,2-diflorobutyl, 2,2-difloropentyl, 3,3-difloropropyl, 3,3-diflorobutyl, 3,3-difloropentyl, 4,4-diflorobutyl, 4,4-difloropentyl or 5,5-difloropentyl group; or an alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group.

W, W$^1$ and W$^2$, independently from each other, denote H, F, Cl or CH$_3$.

X denotes a CN, F, Cl, CF$_3$, CF$_2$Cl, CHFCl, OCF$_3$, OCHF$_2$, OCF$_2$Cl, OCHFCl, R or OR group. Y denotes I or F. Z denotes H or F.

The ring structure
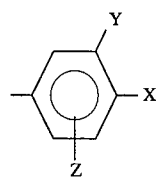
specifically denotes, for example, the following groups:
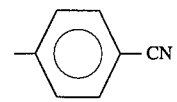
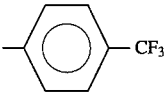
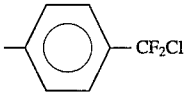
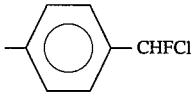
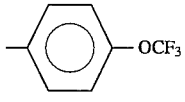
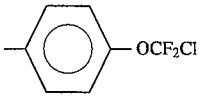
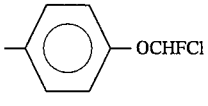
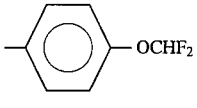
-continued
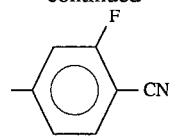
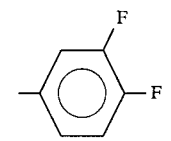
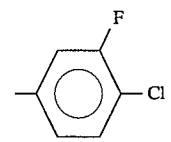
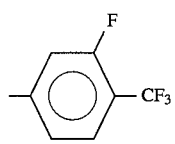
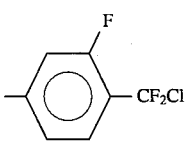
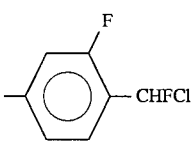
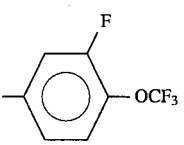
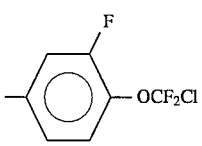
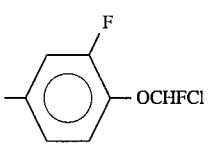
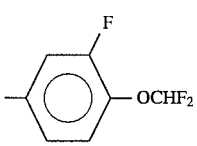
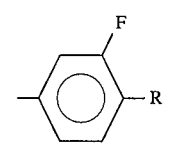

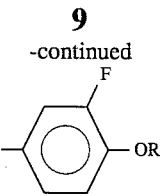
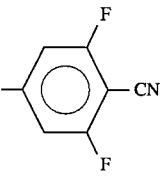
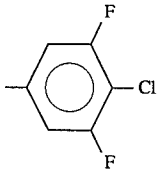
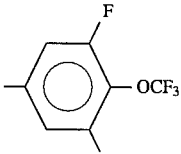
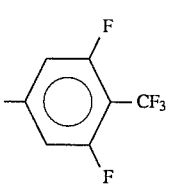
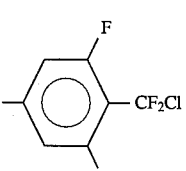
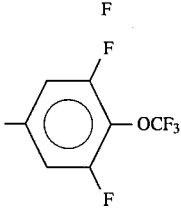
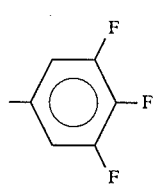
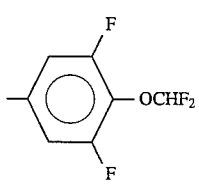

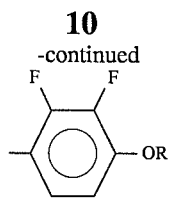

and

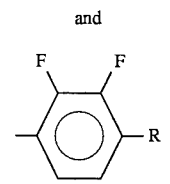

Of these, as far as the ring structure is concerned, compounds

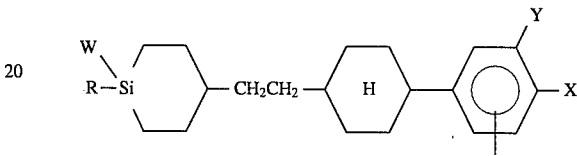

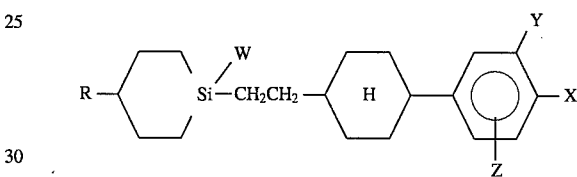

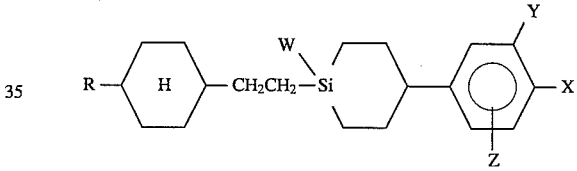

and

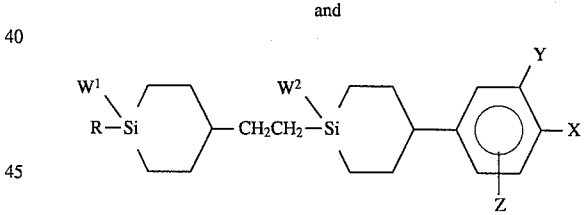

are desirable for practical use.

For R, the following groups are desirable for practical use: a linear-chain alkyl group with a carbon number of 2–7, i.e. an ethyl, n-propyl, n-butyl, n-pentyl, n-hexyl or n-heptyl group; or some branched-chain alkyl groups with a carbon number of 3–7 including isopropyl, 1-methylpropyl, 2-methylpropyl, 1-methylbutyl, 2-methylbutyl, 3-methylbutyl, 1-methylpentyl, 2-methylpentyl and 2-ethylhexyl groups; or an alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group; or some floroalkyl groups with a carbon number of 1–10 in which one or two hydrogen atoms are substituted by florine atom(s) including 2-floroethyl, 2-floropropyl, 4-florobutyl, 4-floropentyl, 5-floropentyl, 1,1-difloroethyl, 2,2-difloroethyl, 2,2-difloropropyl, 2,2-diflorobutyl, 4,4-diflorobutyl and 4,4-difloropentyl groups; or some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups.

H, F and CH$_3$ groups are desirable in practical use for W, W$^1$ and W$^2$.

The groups

-continued
and

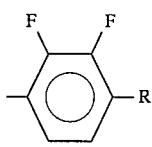

are desirable in practical use for the ring structure

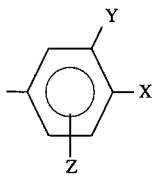

These compounds are prepared by carbon-carbon bond formation or carbon-silicon bond formation between an organometallic reagent and a compound which has an eliminatable group(s) such as a halogen atom, alkoxy, methanesulfonyl, benzenesulfonyl or p-toluenesulfonyl group. Methods of preparing these compounds are described in detail below.

First, a preferred embodiment of a method of preparing a silacyclohexane compound using a reaction between an organometallic reagent R-M and a compound

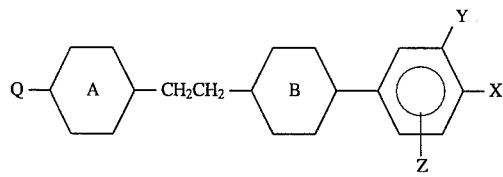

is described below. (In these formulas, M denotes MgP (P denotes a halogen atom), ZnP or Li. R denotes hydrogen, a linear-chain alkyl group with a carbon number of 1 10, a branched-chain alkyl group with a carbon number of 3–8, an alkoxyalkyl group with a carbon number of 2–7, a floroalkyl group with a carbon number of 1–10 in which one or two hydrogen atoms are are substituted by florine atom(s), or an alkenyl group with a carbon number of 2–8. Q denotes a halogen atom, alkoxy, methanesulfonyl, benzenesulfonyl or p-toluenesulfonyl group. X denotes a CN, F, Cl, $CF_3$, $CF_2Cl$, $CHFCl$, $OCF_3$, $OCHF_2$, $OCF_2Cl$, $OCHFCl$, R or OR group. Y denotes H or F. Z denotes H or F.)

In this preparation method, when the group

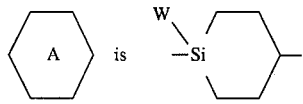

(where W denotes H, F Cl or $CH_3$), Q is a halogen atom or an alkoxy group. Particularly, if Q is a Cl or Br atom, or an $OCH_3$ or $OCH_2CH_3$ group, then the carbon-silicon bond formation reaction proceeds easily and gives a high yield of the target product.

When the group

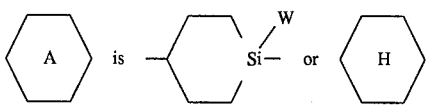

the carbon-carbon bond formation reaction is carried out in the presence of a copper salt. In this case, Q is a halogen atom or a methanesulfonyl, benzenesulfonyl or p-toluenesulfonyl group. It is particularly preferable if Q is Br or I, because then the target product can be obtained with a high yield.

Next, a preferred embodiment of a method of preparing a silacyclohexane compound using a reaction between an organometallic reagent

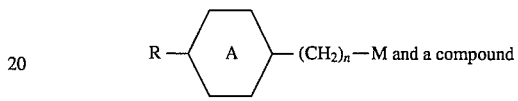

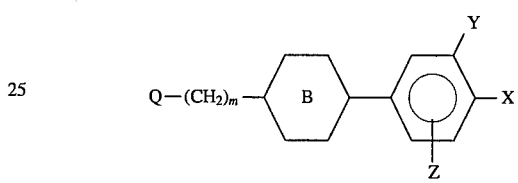

or a reaction between the compounds

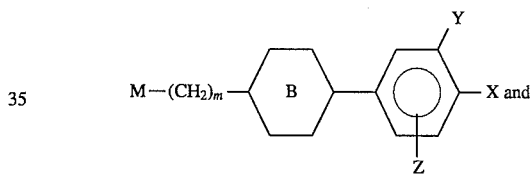

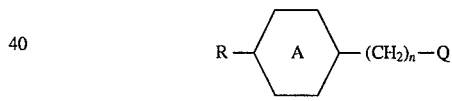

is described below. (In these formulas, M denotes MgP (P denotes a halogen atom), ZnP or Li. R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. Q denotes a halogen atom, alkoxy, methanesulfonyl, benzenesulfonyl or p-toluenesulfonyl group. X denotes a CN, F, Cl, $CF_3$, $CF_2Cl$, $CHFCl$, $OCF_3$, $OCHF_2$, $OCF_2Cl$, $OCHFCl$, R or OR group. Y denotes H or F. Z denotes H or F. n and m are integers 0, 1 or 2 (where n+m=2).)

In these reactions, the carbon-carbon bond formation reaction is carried out in the presence of a catalytic quantity of a copper salt. For Q, a halogen atom or a methanesulfonyl, benzensulfonyl or p-toluenesulfonyl group can be used. Particularly preferable are Br, I and the p-toluenesulfonyl group because they give a higher yield of the target product.

Next, a preferred embodiment of a method of preparing a silacyclohexane compound using a reaction between an organometallic reagent

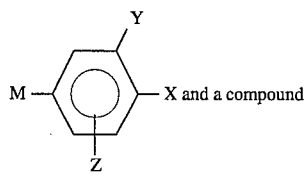

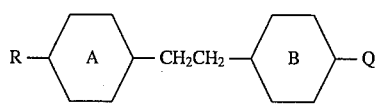

is described below. (In these formulas, M denotes MgP (P denotes a halogen atom), ZnP or Li. R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of 2–8. Q denotes a halogen atom, or an alkoxy, methanesulfonyl, benzenesulfonyl or p-toluenesulfonyl group. X denotes a CN, F, Cl, $CF_3$, $CF_2Cl$, $CHFCl$, $OCF_3$, $OCHF_3$, $OCF_2Cl$, $OCHFCl$, R or OR group. Y denotes H or F. Z denotes H or F.)

In this preparation method, when the group

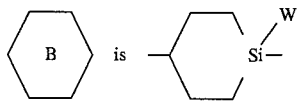

(where W denotes H, F Cl or $CH_3$), Q is a halogen atom or an alkoxy group. It is particularly preferable if Q is a Cl or Br atom, or an $OCH_3$ or $OCH_2CH_3$ group, because then the carbon-silicon bond formation reaction proceeds easily and gives a high yield of the target product.

Also, when the group

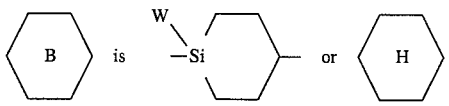

the carbon-carbon bond formation reaction is carried out in the presence of a copper salt. In this case, Q is a halogen atom or a methanesulfonyl, benzenesulfonyl or p-toluenesulfonyl group. It is particularly preferable if Q is Br, I or the p-toluenesulfonyl group, because then the target product can be obtained with a high yield.

Next, a preferred embodiment of a method of preparing a silacyclohexane compound using a reaction between an organometallic reagent

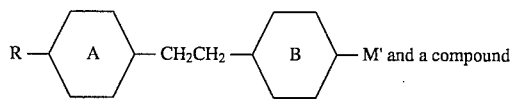

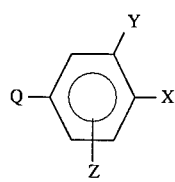

is described below. {In these formulas, M' denotes MgP (P denotes a halogen atom), ZnP or B(OY') (Y' denotes H or an alkyl group). R denotes hydrogen, a linear-chain alkyl group with a carbon number of 1–10, a branched-chain alkyl group with a carbon number of 3–8, an alkoxyalkyl group with a carbon number of 2–7, a fluoroalkyl group with a carbon number of 1–10 in which one or two hydrogen atoms are substituted by florine atom(s), or an alkenyl group with a carbon number of 2–8. Q denotes a halogen atom, or an alkoxy, methanesulfonyl or p-toluenesulfonyl group. X denotes a CN, F, Cl, $CF_3$, $CF_2Cl$, $CHFCl$, $OCF_3$, $OCHF_2$, $OCF_2Cl$, $OCHFCl$, R or OR group. Y denotes H or F. Z denotes H or F.}

This reaction is carried out in the presence of a transition metal catalyst. Palladium compounds and nickel compounds are particularly preferable for the catalyst. Q is a halogen atom or a methanesulfonyl, benzenesulfonyl or p-toluenesulfonyl group. Particularly preferable are Cl, Br and I because they give a higher yield of the target product.

The compound produced here may be a mixture of trans isomers and cis isomers in terms of the conformation of the silacyclohexane ring. If this is the case, then a conventional purification means such as chromatography and recrystallization is employed to separate and purify the trans isomers to obtain the silacyclohexane compound of this invention represented by the general formula (I).

The silacyclohexane compound of this invention can be mixed with known compounds to obtain a liquid crystal composition. The compound used for mixing to obtain the liquid crystal compound can be chosen from among the known compounds shown below:

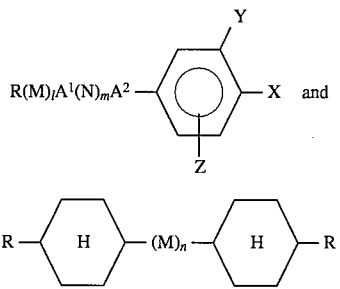

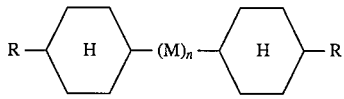

In the above formulas, (M) and (N) denote one of the following:
1) A trans-1,4-cyclohexylene group which has no substitution or which has one or more substitutional groups such as F, Cl, Br, CN or alkyl groups,
2) A ring comprising a cyclohexane ring in which O or S is substituted for one or nonadjacent two $CH_2$ groups,
3) A 1,4-cyclohexenylene group,
4) A 1,4-phenylene group which has no substitution or which has one or two substitutional groups such as F, Cl, $CH_3$ or CN groups, or
5) A ring comprising a 1,4-phenylene group in which an N atom is substituted for one or two CH groups.

$A^1$ and $A^2$ denote $—CH_2CH_2—$, $—CH=CH—$, $—C\equiv C—$, $—CO_2—$, $—OCO—$, $—CH_2O—$, $—OCH_2—$ or a single bond.

l, m=0, 1 or 2 (where l+m=1, 2 or 3, and n=0, 1 or 2)

R denotes hydrogen, a linear-chain alkyl group with a carbon number of 1–10, a branched-chain alkyl group with a carbon number of 3–8, an alkoxyalkyl group with a carbon number of 2–7, a floroalkyl group with a carbon number of 1–10 in which one or two hydrogen atoms are substituted by florine atom(s), or an alkenyl group with a carbon number of X, Y and Z are the same as defined for the general formula (I).

In the above description, if l or n=2, then (M) can contain heterogeneous rings, and if m=2, then (N) can contain heterogeneous rings.

The ratio of one or more types of the silacyclohexane compound of this invention contained in the liquid crystal composition is 1–50 wt %, more preferably 5–30 wt %. The liquid crystal composition can also contain a polygenetic dye(s) to generate the colored guest-host system and additives to change the dielectric anisotropy, viscosity and the orientation of the nematic phase.

The liquid crystal composition thus formed can be used to manufacture various liquid crystal display elements in conventional methods. That is, the liquid crystal composition containing the silacyclohexane compound of this invention is sealed between transparent plates which have electrodes of desired shapes and thus used as liquid crystal display elements. These elements can have various undercoatings, overcoatings for orientation control, a polarizer plate(s), a filter(s) and a reflector layer(s), as necessary. They can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the guest-host (GH) method, the super twisted nematic (STN) method and the polymer dispersion liquid crystal (PDLC) method can be adopted.

EXAMPLES

The details of this invention are described below by referring to specific examples.

[EXAMPLE 1]

(Preparation of trans-4-(2-(trans-4-(3,
4-difluorophenyl)
cyclohexyl)eth-yl)-1-n-propyl-1-silacyclohexane)

A mixed solution of 3.7 g (10 mmol) of 1-chloro-4-(2-(trans-4-(3,4-difluorophenyl)cyclohexyl)ethyl)-1-silacyclohexane and 30 ml of tetrahydrofuran (hereafter abbreviated as "THF") was prepared, and a 5 ml THF solution of 2.5M n-propylmagnesium chloride (12.5 mmol) was dripped into this solution. The silacyclohexane rings of the target product thus obtained were a mixture of trans isomers and cis isomers. Following a conventional after treatment, they were separated by means of chromatography to obtain 2.9 g of the trans isomers of the target product (yield 80%). The results of its analysis are shown below.

IR (liquid film) $v_{max}$: 2922, 2850, 2100, 1606, 1518, 1288, 887 and 815 cm$^{-1}$.

C-N transition temperature: 11.2° C., N-I transition temperature: 63.5° C.

As shown above, it was confirmed that this product exhibited the nematic phase in the temperature range of 11.2° C.–63.5° C., and that the temperature range of the nematic phase was extended significantly on the low temperature end compared with the existing trans-4-(2-(trans-4-(3,4-difluorophenyl)cyclohexyl) ethyl)-1-n-propyl-1-cyclohexane (C-N transition temperature 36.0° C.).

[EXAMPLE 2]

(Preparation of trans-1-n-propyl-4-(2-(trans-4-(3,4,5-trifluorophenyl)cyclohexyl)ethyl)-1-silacyclohexane)

The preparation was conducted in the same manner as in Example 1, except that 3.8 g (10 mmol) of 1-chloro-4-(2-(trans-4-(3,4,5-trifluorophenyl)cyclohexyl)ethyl)-1-silacyclohexane was used instead of 3.7 g (10 mmol) of 1-chloro-4-(2-(trans-4-(3,4-difluorophenyl)cyclohexyl)ethyl)-1-silacyclohexane.

[EXAMPLE 3]

(Preparation of trans-1-n-propyl-4-(2-(trans-4-(p-trifluoromethoxyphenyl)cyclohexyl)ethyl)-1-fluoro-1-silacyclohexane)

The preparation was conducted in the same manner as in Example 1, except that 4.1 g (10 mmol) of 1,1-difluoro-4-(2-(trans-4-(p-trifluoromethoxyphenyl)cyclohexyl)ethyl)-1-silacyclohexane was used instead of 3.7 g (10 mmol) of 1-chloro-4-(2-(trans-4-(3,4-difluorophenyl)cyclohexyl)ethyl)-1-silacyclohexane.

[EXAMPLE 4]

(Preparation of trans-1-n-propyl-4-(2-(trans-4-(p-trifluoromethoxyphenyl)cyclohexyl)ethyl)-1-silacyclohexane)

The preparation was conducted in the same manner as in Example 1, except that 3.9 g (10 mmol) of 1-chloro-4-(2-(trans-4-(p-trifluoromethoxyphenyl)cyclohexyl)ethyl)-1-silacyclohexane was used instead of 3.7 g (10 mmol) of 1-chloro-4-(2-(trans-4-(3,4-difluorophenyl)cyclohexyl)ethyl)-1-silacyclohexane.

IR (liquid film) $v_{max}$: 2922, 2850, 2100, 1510, 1261, 1223, 1167 and 842 cm$^{-1}$.

C-N transition temperature: 31.5° C., N-I transition temperature: 84.9° C.

[EXAMPLE 5]

(Preparation of trans-4-(2-(trans-4-(4-chloro-3-fluorophenyl)cyclohexyl) ethyl)-1-n-propyl-1-silacyclohexane)

The preparation was conducted in the same manner as in Example 1, except that 3.7 g (10 mmol) of 1-chloro-4-(2-(trans-4-(4-chloro-3-fluorophenyl)cyclohexyl)ethyl-1-silacyclohexane was used instead of 3.7 g (10 mmol) of 1-chloro-4-(2-(trans-4-(3,4-difluorophenyl)cyclohexyl)ethyl)-1-silacyclohexane.

[EXAMPLE 6]

(Preparation of trans-4-(2-(trans-4-(p-fluorophenyl)cyclohexyl)ethyl)-1-n-pentyl-1-silacyclohexane)

A 15 ml THF solution of 2.5M n-pentylzinc chloride (37.5 mmol) (prepared from a corresponding Grignard's reagent and zinc chloride) was dripped into a mixed solution of 7.0 g (21 mmol) of 1-chloro-4-(2-(trans-4-(p-fluorophenyl)cyclohexyl) ethyl)-1-silacyclohexane and 60 ml of THF. The silacyclohexane rings of the target product thus obtained were a mixture of trans isomers and cis isomers. Following a conventional after treatment, they were separated by means of chromatography to obtain 5.9 g of the trans isomers of the target product (yield 75%). The results of its analysis are shown below.

IR (KBr) $v_{max}$: 2916, 2848, 2102, 1508, 1221, 1159, 885 and 833 cm$^{-1}$

C-N transition temperature: 44.3° C., N-I transition temperature: 83.8° C.

[EXAMPLE 7]

(Preparation of trans-4-(2-(trans-4-(p-fluorophenyl)cyclohexyl) ethyl)-1-ethyl-1-silacyclohexane)

The preparation was conducted in the same manner as in Example 6, except that ethylzinc chloride was used instead of n-pentylzinc chloride.

IR (KBr) $v_{max}$: 2914, 2850, 2110, 1508, 1219, 825, 814 and 766 cm$^{-1}$

C-N transition temperature: 62.5° C., N-I transition temperature: 77.9° C.

[EXAMPLE 8]

(Preparation of trans-4-(2-(trans-4-(3,4-difluorophenyl)cyclohexyl) ethyl)-1-ethyl-1-silacyclohexane)

The preparation was conducted in the same manner as in Example 6, except that 7.5 g (21 mmol) of 1-chloro-4-(2-(trans-4-(3,4-difluorophenyl)cyclohexyl)ethyl)-1-silacyclohexane and ethylzinc chloride were used instead of 7.0 g (21 mmol) of 1-chloro-4-(2-(trans-4-(p-fluorophenyl)cyclohexyl)ethyl)- 1-silacyclohexane and n-pentylzinc chloride.

IR (liquid film) $v_{max}$: 2920, 2850, 2098, 1518, 1290, 288, 887, 816 and 769 cm$^{-1}$ C-N transition temperature: 33.4° C., N-I transition temperature: 48.4° C.

[EXAMPLE 9]

(Preparation of trans-4-(2-(trans-4-(p-chlorophenyl) cyclohexyl) ethyl)-1-n-pentyl-1-silacyclohexane)

The preparation was conducted in the same manner as in Example 6, except that 7.5 g (21 mmol) of 1-chloro-4-(2-(trans-4-(p-chlorophenyl)cyclohexyl)ethyl)-1-silacyclohexane was used instead of 7.0 g (21 mmol) of 1-chloro-4-(2-(trans-4 (p-fluorophenyl)cyclohexyl)ethyl)-1-silacyclohexane.

IR (KBr) $v_{max}$: 2916, 2846, 2096, 1493, 1092, 889 and 818 cm$^{-1}$

C-N transition temperature: 35.9° C., N-I transition temperature: 99.5° C.

[EXAMPLE 10]

(Preparation of trans-4-(2-(trans-4-(p-cyanophenyl)cyclohexyl) ethyl)-1-n-pentyl-1-silacyclohexane)

The preparation was conducted in the same manner as in Example 6, except that 7.3 g (21 mmol) of 1-chloro-4-(2-(trans-4-(p-cyanophenyl)cyclohexyl)ethyl)-1-silacyclohexane was used instead of 7.0 g (21 mmol) of 1-chloro-4-(2-(trans- 4-(p-fluorophenyl)cyclohexyl)ethyl)-1-silacyclohexane.

[EXAMPLE 11]

(Preparation of trans-4-(2-(trans-4-(2,3-difluoro-4-ethoxyphenyl) cyclohexyl)ethyl)-1-n-pentyl-1-silacyclohexane)

The preparation was conducted in the same manner as in Example 6, except that 8.4 g (21 mmol) of 1-chloro-4-(2-(trans-4-(2,3-difluoro-4-ethoxyphenyl)cyclohexyl)ethyl)-1-silacyclohexane was used instead of 7.0 g (21 mmol) of 1-chloro- 4-(2-(trans-4-(p-fluorophenyl)cyclohexyl)ethyl)-1-silacyclohexane.

[EXAMPLE 12]

(Preparation of trans-4-(2-(trans-4-(8,5-difluoro-4-difluoromethoxyphenyl)cyclohexyl)ethyl)-1-n-pentyl-1-silacyclohexane)

The preparation was conducted in the same manner as in Example 6, except that 8.9 g (21 mmol) of 1-chloro-4-(2-(trans-4-(3,5-difluoro-4-difluoromethoxyphenyl)cyclohexyl)ethyl)- 1-silacyclohexane was used instead of 7.0 g (21 mmol) of 1-chloro-4-(2-(trans-4-(p-fluorophenyl)cyclohexyl)ethyl)-1-silacyclohexane.

[EXAMPLE 13]

(Preparation of trans-4-(2-(trans-4-(p-trifluoromethylphenyl) cyclohexyl) ethyl)-1-n-propyl-1-silacyclohexane)

The preparation was conducted in the same manner as in Example 6, except that 8.2 g (21 mmol) of 1-chloro-4-(2-(trans-4-(p-trifluoromethylphenyl)cyclohexyl)ethyl)-1-silacyclohexane and n-propylzinc chloride were used instead of 7.0 g (21 mmol) of 1-chloro-4-(2-(trans-4-(p-fluorophenyl)cyclohexyl)- 1-silacyclohexane and n-pentylzinc chloride.

[EXAMPLE 14]

(Preparation of trans-4-(2-(trans-4-(3, 5-difluoro-4-chlorophenyl) cyclohexyl) ethyl)-1-n-pentyl-1-silacyclohexane)

The preparation was conducted in the same manner as in Example 6, except that 8.2 g (21 mmol) of 1-chloro-4-(2-(trans-4-(3,5-difluoro-4-chlorophenyl)cyclohexyl)ethyl)-1-silacyclohexane was used instead of 7.0 g (21 mmol) of 1-chloro-4-(2-(trans-4-(p-fluorophenyl)cyclohexyl)ethyl)-1-silacyclohexane.

[EXAMPLE 15]

(Preparation of trans-4-(2-(trans-4-(3,4-difluorophenyl) cyclohexyl)ethyl)-1-(4-pentenyl)-1-silacyclohexane)

The preparation was conducted in the same manner as in Example 6, except that 7.5 g (21 mmol) of 1-chloro-4-(2-(trans-4-(3,4-difluorophenyl)cyclohexyl)ethyl)-1-silacyclohexane and 4-pentenylzinc chloride were used instead of 7.0 g (21 mmol) of 1-chloro-4-(2-(trans-4-(p-fluorophenyl)cyclohexyl) ethyl)-1-silacyclohexane and n-pentylzinc chloride.

[EXAMPLE 16]

(Preparation of
trans-4-(2-(trans-4-(3,4-difluorophenyl) cyclohexyl)
ethyl)-1-(3-methoxypropyl)-1-silacyclohexane)

The preparation was conducted in the same manner as in Example 6, except that 7.5 g (21 mmol) of 1-chloro-4-(2-(trans-4-(3,4-difluorophenyl)cyclohexyl)ethyl)-1-silacyclohexane and 3-methoxypropylzinc chloride were used instead of 7.0 g (21 mmol) of 1-chloro-4-(2-(trans-4-(p-fluorophenyl)cyclohexyl) ethyl)-1-silacyclohexane and n-pentylzinc chloride.

[EXAMPLE 17]

(Preparation of
trans-4-(2-(trans-4-(3,4-difluorophenyl) cyclohexyl)
ethyl)-1-(3-methylbutyl)-1-silacyclohexane)

The preparation was conducted in the same manner as in Example 6, except that 7.5 g (21 mmol) of 1-chloro-4-(2-(trans-4-(3,4-difluorophenyl)cyclohexyl)ethyl)-1-silacyclohexane and 3-methylbutylzinc chloride were used instead of 7.0 g (21 mmol) of 1-chloro-4-(2-(trans-4-(p-fluorophenyl)cyclohexyl) ethyl)-1-silacyclohexane and n-pentylzinc chloride.

[EXAMPLE 18]

(Preparation of
trans-1-(2-(trans-4-n-butylcyclohexyl)ethyl)-
4-(3,4-difluorophenyl)-1-silacyclohexane)

A 55 ml THF solution of 2.0M 2-(trans-4-n-butylcyclohexyl) ethylmagnesium bromide (110 mmol) was dripped into a mixed solution of 24.6 g (100 mmol) of 1-chloro-4-(3,4-difluorophenyl)- 1-silacyclohexane and 250 ml of THF. The silacyclohexane rings of the target product thus obtained were a mixture of trans isomers and cis isomers. Following a conventional after treatment, they were separated by means of chromatography to obtain 28.3 g of the trans isomers of the target product (yield 75). The results of its analysis are shown below.

IR (liquid film) $v_{max}$: 2918, 2850, 2102, 1608, 1518, 1213, 889 and 812 cm$^{-1}$.

C-N transition temperature: 6.2° C., N-I transition temperature: 37.7° C.

As shown above, it was confirmed that this product exhibited the nematic phase in the temperature range of 6.2° C.–37.7° C., and that the temperature range of the nematic phase was extended significantly on the low temperature end compared with the existing trans-1-(2-(trans-4-n-butylcyclohexyl)ethyl)-4-( 3,4-difluorophenyl)-1-cyclohexane (C-N transition temperature 32.0° C.).

[EXAMPLE 19]

(Preparation of
trans-1-(2-(trans-4-ethylcyclohexyl)ethyl)-
4-p-fluorophenyl-1-silacyclohexane)

The preparation was conducted in the same manner as in Example 18, except that 22.8 g (100 mmol) of 1-chloro-4-(p-fluorophenyl)-1-silacyclohexane and 2-(trans-4-ethylcyclohexyl) ethylmagnesium bromide were used instead of 24.6 g (100 mmol) of 1-chloro-4-(3,4-difluorophenyl)-1-silacyclohexane and 2-(trans-4-n-butylcyclohexyl)ethyl- magnesium bromide.

IR (liquid film) $v_{max}$: 2916, 2850, 2100, 1510, 1228, 985, 887, 812 and 787 cm$^{-1}$.

C-I transition temperature: 35.3° C.

[EXAMPLE 20]

(Preparation of
trans-1-(2-(trans-4-ethylcyclohexyl)ethyl)-
4-(3,4-difluorophenyl)-1-silacyclohexane)

The preparation was conducted in the same manner as in Example 18, except that 2-(trans-4-ethylcyclohexyl) ethylmagnesium bromide was used instead of 2-(trans-4-n-butylcyclohexyl) ethylmagnesium bromide.

IR (liquid film) $v_{max}$: 2916, 2880, 2100, 1608, 1518, 1286, 1213, 1115, 987, 889, 812 and 769 cm$^{-1}$.

C-N transition temperature: 13.3° C., N-I transition temperature: 19.5° C.

[EXAMPLE 21]

(Preparation of
trans-1-(2-(trans-4-n-propylcyclohexyl)ethyl)-
4-(3,4-difluorophenyl)-1-silacyclohexane)

The preparation was conducted in the same manner as in Example 18, except that 2-(trans-4-n-propylcyclohexyl)ethylmagnesium bromide was used instead of 2-(trans-4-n-butylcyclohexyl) ethylmagnesium bromide.

IR (liquid film) $v_{max}$: 2916, 2848, 2102, 1608, 1518, 1284, 1213, 889, 812 and 769 cm$^{-1}$.

C-N transition temperature: 20.1° C., N-I transition temperature: 34.0° C.

[EXAMPLE 22]

(Preparation of
trans-4-(2-(trans-4-(p-fluorophenyl)cyclohexyl)
ethyl)-1-n-propyl-1-silacyclohexane)

A 30 ml THF solution of 2.0 M (trans-4-n-propyl-4-silacyclohexyl)methylmagnesium bromide (60 mmol) was dripped into a mixed solution of 18.1 g (50 mmol) of (trans-4-(p-fluorophenyl) cyclohexyl)methyl p-toluenesulfonate and 150 ml of THF. The silacyclohexane rings of the target product thus obtained were a mixture of trans isomers and cis isomers. Following a conventional after treatment, they were separated by means of chromatography to obtain 12.4 g of the trans isomers of the target product (yield 72%). The results of its analysis are shown below.

IR (KBr) $v_{max}$: 2916, 2848, 2106, 1508, 1221, 885 and 883 cm$^{-1}$

C-N transition temperature: 43.9° C., N-I transition temperature: 93.8° C.

[EXAMPLE 23]

(Preparation of
trans-1-n-pentyl-4-(2-(trans-4-(p-methoxyphenyl)
cyclohexyl) ethyl)-1-silacyclohexane)

The preparation was conducted in the same manner as in Example 22, except that 18.7 g (50 mmol) of (trans-4-(p-methoxyphenyl)cyclohexyl)methyl p-toluenesulfonate and (trans-4-n-pentyl-4-silacyclohexyl)methylmagnesium bromide were used instead of 18.1 g (50 mmol) of (trans-4-(p- fluorophenyl cyclohexyl)methyl p-toluenesulfonate and (trans-4-n-propyl- 4-silacyclohexyl)methylmagnesium bromide.

[EXAMPLE 24]

(Preparation of
trans-4-(2-(trans-4-(3-fluoro-4-trifluoro
methoxyphenyl)cyclohexyl)ethyl)-1-n-pentyl-1-
silacyclohexane)

The preparation was conducted in the same manner as in Example 22, except that 22.9 g (50 mmol) of (trans-4-(3-fluoro-4-trifluoromethoxyphenyl)cyclohexyl)methyl p-toluenesulfonate and (trans-4-n-pentyl-4-silacyclohexyl)methylmagnesium bromide were used instead of 18.1 g (50 mmol) of (trans-4-(p-fluorophenyl) cyclohexyl)methyl p-toluenesulfonate and (trans-4-n-propyl- 4-silacyclohexyl)methylmagnesium bromide.

[EXAMPLE 25]

(Preparation of
trans-4-(p-fluorophenyl)-1-(2-(trans-4-n-pentyl-
4-silacyclohexyl)ethyl)-1-silacyclohexane)

The preparation was conducted in the same manner as in Example 22, except that 18.9 g (50 mmol) of (trans- 4-(p-fluorophenyl)-1-silacyclohexyl)methyl p-toluenesulfonate and (trans-4-n-pentyl-4-silacyclohexyl)methylmagnesium bromide were used instead of 18.1 g (50 mmol) of (trans-4-(p-fluorophenyl) cyclohexyl)methyl p-toluenesulfonate and (trans-4-n-propyl 4-silacyclohexyl)methylmagnesium bromide.

[EXAMPLE 26]

(Preparation of trans-1-(2-(trans-4-(3,
4-difluorophenyl) cyclohexyl)
ethyl)-4-n-pentyl-1-silacyclohexane)

A 35 ml THF solution of 1.5M 2-(trans-d-(3, 4-difluorophenyl) cyclohexyl)ethyl lithium (52.5 mmol) was dripped into a mixed solution of 10.0 g (50 mmol) of 1-methoxy-4-n-pentyl-1-silacyclohexane and 100 ml of THF. The silacyclohexane rings of the target product thus obtained were a mixture of trans isomers and cis isomers. Following a conventional after treatment, they were separated by means of chromatography to obtain 12.9 g of the trans isomers of the target product (yield 69%). The results of its analysis are shown below.

IR (liquid film) $v_{max}$: 2920, 2850, 2098, 1608, 1518, 1288, 1286, 887, 862 and 816 cm$^{-1}$.

C-N transition temperature: 14.7 °C., N-I transition temperature: 28.9° C.

As shown above, it was confirmed that this product exhibited the nematic phase in the temperature range of 14.7° C.–28.9° C., and that the temperature range of the nematic phase was extended significantly on the low temperature end compared with the existing trans-1-(2-(trans-4 (3,4-difluorophenyl)cyclohexyl) ethyl)-4-n-pentyl-1-cyclohexane (C-N transition temperature 38.0° C.).

[EXAMPLE 27]

(Preparation of
trans-4-(2-(trans-4-(3,4-difluorophenyl)cyclohexyl)
ethyl)-1-n-pentyl-1-silacyclohexane)

The preparation was conducted in the same manner as in Example 26, except that 17.4 g (50 mmol) of trans-4-(2-(trans- 4-(3,4-difluorophenyl)cyclohexyl)ethyl)-1-methoxy-1-silacyclohexane and n-pentyl lithium were used instead of 10.0 g (50 mmol) of 1-methoxy-4-n-pentyl-1-silacyclohexane and 2-(trans-4-(3, 4-difluorophenyl)cyclohexyl)ethyl lithium.

IR (liquid film) $v_{max}$: 2920, 2850, 2098, 1608, 1518, 1290, 1286 and 816 cm$^{-1}$ C-N transition temperature: 8.0° C., N-I transition temperature: 66.1° C.

[EXAMPLE 28]

(Preparation of
trans-1-(2-(trans-4-n-butylcyclohexyl)ethyl)-
4-n-(p-fluorophenyl)-1-silacyclohexane)

The preparation was conducted in the same manner as in Example 26, except that 11.2 g (50 mmol) of trans-4-(p-fluorophenyl)- 1-methoxy-1-silacyclohexane and 2-(trans-4-n-butylcyclohexyl) ethyl lithium were used instead of 10.0 g (50 mmol) of 1-methoxy- 4-n-pentyl-1-silacyclohexane and 2-(trans-4-(3,4-difluorophenyl) cyclohexyl)ethyl lithium.

IR (liquid film) $v_{max}$: 2918, 2850, 2102, 1605, 1510, 1228, 985, 887, 881 and 812 cm$^{-1}$ S-N transition temperature: 20.7° C., C-N transition temperature: 22.0° C., N-] transition temperature: 74.6° C.

[EXAMPLE 29]

(Preparation of
trans-4-(p-fluorophenyl)-1-(2-(trans-4-n-
pentylcyclohexyl) ethyl)-1-silacyclohexane)

The preparation was conducted in the same manner as in Example 26, except that 11.2 g (50 mmol) of trans-4-(p-fluorophenyl)- 1-methoxy-1-silacyclohexane and 2-(trans-4-n-pentylcyclohexyl) ethyl lithium were used instead of 10.0 g (50 mmol) of 1-methoxy- 4-n-pentyl-1-silacyclohexane and 2-(trans-4-(3,4-difluorophenyl) cyclohexyl)ethyl lithium.

IR (KBr) $v_{max}$: 2918, 2848, 2102, 1510, 1232, 887, 881 and 816 cm$^{-1}$

C-S transition temperature: 25.4° C., S-N transition temperature: 32.5° C., N-I transition temperature: 82.0° C.

[EXAMPLE 30]

(Preparation of
4-(p-fluorophenyl)-1-(2-(trans-4-n-propylcyclohexyl)
ethyl)-1-silacyclohexane)

A 25 ml THF solution of 1.0M (4-(p-fluorophenyl)-1-silacyclohexyl methylmagnesium chloride (25 mmol) was dripped into a mixed solution of 4.5 g (19.9 mmol) of trans-1-iodomethyl- 4-n-propylcyclohexane, 10 mg of copper iodide (I), 50 mg of triethyl phosphite and 50 ml of THF. The silacyclohexane rings of the target product thus obtained were a mixture of trans isomers and cis isomers. Following a conventional after treatment, they were separated by means of chromatography to obtain 5.7 g of the trans isomers of the target product (yield 82.9%). The results of its analysis are shown below.

IR (KBr) $v_{max}$: 2908, 2848, 2096, 1510, 1223, 985, 887, 831, 814 and 735 cm$^{-1}$ C-N transition temperature: 49.1° C., N-I transition temperature: 69.2° C.

[EXAMPLE 31]

(Preparation of 4-(3,4-difluorophenyl)-1-(2-(trans-4-n-pentylcyclohexyl)ethyl)-1-silacyclohexane)

The preparation was conducted in the same manner as in Example 30, except that 5.9 g (19.9 mmol) of trans-1-iodomethyl- 4-n-pentylcyclohexane and (4-(3,4-difluorophenyl)-1-silacyclohexyl) methylmagnesium chloride were used instead of 4.5 g (19.9 mmol) of trans-1-iodomethyl-4-n-propylcyclohexane and (4-(p-fluorophenyl)- 1-silacyclohexyl)methylmagnesium chloride.

IR (KBr) $v_{max}$: 2920, 2848, 2106, 1518, 1215, 1115, 987, 889, 812 and 768 cm$^{-1}$ C-N transition temperature: 33.3° C., N-I transition temperature: 60.0° C.

[EXAMPLE 32]

(Preparation of trans-4-isobutyl-1-(2-(trans-4-(p-fluorophenyl)cyclohexyl)ethyl)-1-silacyclohexane)

The preparation was conducted in the same manner as in Example 30, except that 6.3 g (19.9 mmol) of trans-1-iodomethyl- 4-(p-fluorophenyl)cyclohexane and (4-n-isobutyl-1-silacyclohexyl) methylmagnesium chloride were used instead of 4.5 g (19.9 mmol) of trans-1-iodomethyl-4-n-propylcyclohexane and (4-(p-fluorophenyl)- 1-silacyclohexyl)methylmagnesium chloride.

[EXAMPLE 33]

(Preparation of 1-(3,4-difluorophenyl)-4-(2-(trans-4-n-pentylcyclohexyl) ethyl)-1-silacyclohexane)

A 15 ml THF solution of 1.0M 3,4-difluorophenylmagnesium bromide (15 mmol) was dripped into a mixed solution of 2.5 g (7.9 mmol) of 1-chloro-4-(2-(trans-4-n-pentylcyclohexyl) ethyl)-1-silacyclohexane and 50 ml of THF.

The silacyclohexane rings of the target product thus obtained were a mixture of trans isomers and cis isomers. Following a conventional after treatment, they were separated by means of chromatography to obtain 2.0 g of the trans isomers of the target product (yield 64%).

[EXAMPLE 34]

(Preparation of trans-4-(2-(trans-4-(p-n-propylphenyl)cyclohexyl) ethyl)-1-n-propyl-1-silacyclohexane)

The preparation was conducted in the same manner as in Example 33, except that 2.6 g (7.9 mmol) of 1-bromo-4-(2-(trans-4-n-propyl-4-silacyclohexyl)ethyl)cyclohexane and p-n-propylphenylmagnesium bromide were used instead of 2.5 g (7.9 mmol) of 1-chloro-4-(2-(trans-4-n-pentylcyclohexyl) ethyl)-1-silacyclohexane and 3,4-difluorophenyl-magnesium bromide.

[EXAMPLE 35]

(Preparation of trans-1-(3,4-difluorophenyl)-1-methyl-4-( 2-(trans-4-n-pentylcyclohexyl) ethyl)-1-silacyclohexane)

The preparation was conducted in the same manner as in Example 33, except that 2.6 g (7.9 mmol) of 1-chloro-1-methyl- 4-(2-(trans-4-n-pentylsilacyclohexyl)ethyl)-1-silacyclohexane was used instead of 2.5 g (7.9 mmol) of 1-chloro-4-(2-(trans- 4-n-pentylcyclohexyl)ethyl)-1-silacyclohexane.

[EXAMPLE 36]

(Preparation of trans-4-(2-(trans-4-(p-trifluoromethoxyphenyl) cyclohexyl)ethyl)-1-(4-fluorobutyl)-1-silacyclohexane)

The preparation was conducted in the same manner as in Example 33, except that 2.9 g (7.9 mmol) of 1-bromo-4-( 2-(trans-4-(4-fluorobutyl)-4-silacyclohexyl)ethyl)cyclohexane was used instead of 2.5 g (7.9 mmol) of 1-chloro-4-(2-(trans- 4-n-pentylcyclohexyl)ethyl)-1-silacyclohexane and p-trifluoromethoxymagnesium bromide was used instead of 3,4difluorophenylmagnesium bromide.

[EXAMPLE 37]

(Preparation of trans-4-(2-(trans-4-(3,4-difluorophenyl)cyclohexyl) ethyl)-1-(4-fluoropentyl)-1-silacyclohexane)

The preparation was conducted in the same manner as in Example 33, except that 3.0 g (7.9 mmol) of 1-bromo-4-( 2-(trans-4-(4-fluoropentyl)-4-silacyclohexyl)ethyl)cyclohexane was used instead of 2.5 g (7.9 mmol) of 1-chloro-4-(2-(trans- 4-n-pentylcyclohexyl)ethyl)-1-silacyclohexane.

The compounds of this invention obtained in the examples described above were added to existing liquid crystal compositions to prepare liquid crystal compositions of this invention. The transition temperature(s) and the threshold voltage at 25° C. were measured for the obtained liquid crystal compositions.

[EXAMPLE 38]

Mixture A comprising 43 mole % of trans-4-(2-(trans-4-( 3, 4-difluorophenyl)cyclohexyl)ethyl)-1-ethyl-1-silacyclohexane, 17 mole % of trans-4-(2-(trans-4-(3, 4-difluorophenyl)cyclohexyl) ethyl)-1-n-propyl-1-silacyclohexane and 40 mole % of trans-4-( 2-(trans-4-(3,4-difluorophenyl)cyclohexyl)ethyl)-1-n-pentyl- 1-silacyclohexane exhibited the following characteristics:

C-N transition temperature: −10.7° C.

N-I transition temperature: 93.8° C.

Threshold voltage (5 micrometer-cell, 32 Hz): 2.5 V

A mixture comprising 85 mole % of this mixture A and 15 mole % of trans-4-(2-(trans-4-(3,4-difluorophenyl)cyclohexyl) ethyl)-1-n-pentyl-1-silacyclohexane obtained in Example 27 exhibited the following characteristics:

C-N transition temperature: −16.5° C.

N-I transition temperature: 89.6° C.

Threshold voltage (5 micrometer-cell, 32 Hz): 2.35 V

The liquid crystal compounds of this invention which have Si as a ring composing element have the following advantages over liquid crystal compounds which have a conventional CECP structure comprising similar hydrocarbon rings:

(1) Since the nematic phase is extended on the low temperature end, the viscosity in a low temperature range decreases, resulting in the improved response time in the low temperature range.

(2) Mutual solubility in a low temperature range improves.

Also, liquid crystal compounds whose X in the general formula (I) is neither R nor OR have, in addition to the advantages mentioned above, the effect of lowering the threshold voltage because of a greater dielectric anisotropy.

The liquid crystal compounds of this invention, depending on the selection of their substitutional groups, can be widely used as the base material which comprises the major component of the liquid crystal phase, in a manner similar to how the conventional liquid crystal compounds with a CECP structure of similar hydrocarbon rings are used. The liquid crystal compound whose substitutional group X in the general formula (I) is R or OR has negative or near-zero dielectric anisotropy, and therefore it should preferably be used for the liquid crystal phase for display based on the dynamic scattering (DS), guest-host (GH) or deformation of aligned phase (PAP mode). The compounds in which X is other than these should preferably be used for manufacturing the liquid crystal phase with a large positive dielectric anisotropy which is used in display elements based on the twisted nematic cell or the cholesteric-nematic phase transition.

We claim:

1. A silacyclohexane compound represented by the following formula (I):

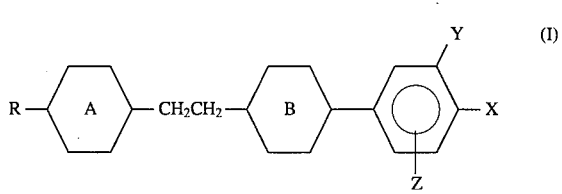

wherein R denotes a hydrogen, a linear-chain alkyl group with a carbon number of 1–10, a branched-chain alkyl group with a carbon number of 3–8, an alkoxyalkyl group with a carbon number of 2–7, a fluoroalkyl group with a carbon number of 1–10 in which one or two hydrogen atoms are substituted by fluorine atom(s), or an alkenyl group with a carbon number of 2–8, and wherein at least one of

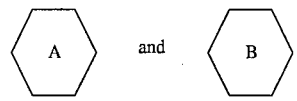

is trans-1-sila-1, 4-cyclohexylene or trans-4-sila-1, 4-cyclohexylene group whose silicon at position 1 or position 4 has a substitutional groups(s) of H, F, Cl or $CH_3$, and the other denotes a trans-1, 4-cyclohexylene group, X denotes a CN, F, Cl $CF_3$, $CF_2Cl$, CHFCl, $OCF_3$, $OCHF_2$, $OCF_2Cl$, OCHFCl, R or OR group, R is the same as defined in formula (1), Y denotes H or F, and Z denotes H or F.

2. A liquid crystal composition comprising the compound of claim 1.

3. A liquid crystal display element comprising the liquid crystal composition of claim 2.

4. A silacyclohexane compounded represented by the following formula (I):

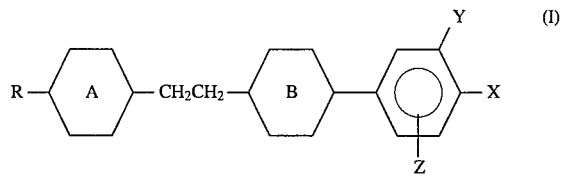

wherein R denotes a hydrogen, a linear-chain alkyl group with a carbon number of 1–10, a branched-chain alkyl group with a carbon number of 3–8, an alkoxyalkyl group with a carbon number of 2–7, a fluoroalkyl group with a carbon number of 1–10 in which one or two hydrogen atoms are substituted by fluorine atom(s), or an alkenyl group with a carbon number of 2–8, and wherein at least one of

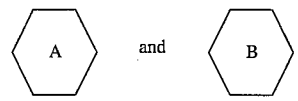

is trans-1-sila-1, 4-cyclohexylene or trans-4-sila-1, 4-cyclohexylene group whose silicon at positions 1 or 4 has a substitutional groups(s) of H, F, Cl or $CH_3$, and the other denotes a trans-1-sila-1,4-cyclohexylene, or a trans-4-sila-1,4-cyclohexylene group, or a trans-1, 4-cyclohexylene group, X denotes a CN, F, Cl $CF_3$, $CF_2Cl$, CHFCl, $OCF_3$, $OCHF_2$, $OCF_2Cl$, OCHFCl, R or OR group, R is the same as defined in formula (I), Y denotes H or F, and Z denotes H or F.

* * * * *